US009056283B2

(12) United States Patent
Yahaya

(10) Patent No.: US 9,056,283 B2
(45) Date of Patent: Jun. 16, 2015

(54) FACILITATED TRANSPORT MEMBRANE FOR THE SEPARATION OF AROMATICS FROM NON-AROMATICS

(71) Applicant: Saudi Arabian Oil Company, Dhahran (SA)

(72) Inventor: Garba O. Yahaya, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 358 days.

(21) Appl. No.: 13/781,881

(22) Filed: Mar. 1, 2013

(65) Prior Publication Data
US 2013/0228515 A1 Sep. 5, 2013

Related U.S. Application Data

(60) Provisional application No. 61/606,080, filed on Mar. 2, 2012.

(51) Int. Cl.
| | |
|---|---|
| *B01D 15/00* | (2006.01) |
| *B01D 63/00* | (2006.01) |
| *B01D 67/00* | (2006.01) |
| *B01D 61/36* | (2006.01) |
| *B01D 53/22* | (2006.01) |
| *B01D 69/14* | (2006.01) |
| *B01D 71/82* | (2006.01) |
| *C07C 7/144* | (2006.01) |
| *B01D 71/08* | (2006.01) |
| *B01D 71/38* | (2006.01) |

(52) U.S. Cl.
CPC ............ *B01D 61/362* (2013.01); *B01D 53/228* (2013.01); *B01D 67/0093* (2013.01); *B01D 69/142* (2013.01); *B01D 71/08* (2013.01); *B01D 71/38* (2013.01); *B01D 71/82* (2013.01); *C07C 7/144* (2013.01); *B01D 2323/30* (2013.01)

(58) Field of Classification Search
CPC ............ B01D 61/362; B01D 2311/04; B01D 2323/30; B01D 67/0093; B01D 69/142; B01D 2311/12; B01D 61/36; B01D 71/08; B01D 2325/36; B01D 71/60; B01D 53/228; B01D 69/10; B01D 67/0088; C07C 7/144; C07C 15/04; C07C 45/786
USPC ............ 210/640, 321.74, 321.6, 490, 500.42; 264/41, 48
See application file for complete search history.

(56) References Cited

U.S. PATENT DOCUMENTS

| | | | |
|---|---|---|---|
| 3,556,991 A * | 1/1971 | Gerhold ........................ 208/321 |
| 3,567,632 A * | 3/1971 | Richter et al. ............. 210/321.6 |
| 3,996,589 A | 12/1976 | Breese |
| 4,115,465 A | 9/1978 | Elfert et al. |
| 4,532,029 A | 7/1985 | Black et al. |
| 4,802,987 A | 2/1989 | Black |
| 4,808,313 A * | 2/1989 | Michizuki et al. ....... 210/500.28 |
| 4,828,773 A | 5/1989 | Feimer et al. |
| 4,879,044 A | 11/1989 | Feimer et al. |
| 4,914,064 A | 4/1990 | Schucker |
| 4,929,357 A | 5/1990 | Schucker |
| 4,929,358 A | 5/1990 | Koenitzer |
| 4,968,430 A | 11/1990 | Hildenbrand et al. |
| 4,976,868 A | 12/1990 | Sartori et al. |
| 4,985,147 A * | 1/1991 | Mochizuki et al. ...... 210/500.27 |
| 5,015,268 A | 5/1991 | Ho |
| 5,019,666 A | 5/1991 | Sartori et al. |
| 5,030,355 A | 7/1991 | Schucker |
| 5,055,631 A | 10/1991 | Sartori et al. |
| 5,055,632 A | 10/1991 | Schucker |
| 5,062,866 A | 11/1991 | Ho |
| 5,063,186 A * | 11/1991 | Schucker ........................ 502/4 |
| 5,177,296 A | 1/1993 | Sartori et al. |
| 5,288,712 A * | 2/1994 | Chen ............................ 210/640 |
| 5,396,019 A | 3/1995 | Sartori et al. |
| 5,498,823 A * | 3/1996 | Noble et al. .................. 585/818 |

(Continued)

FOREIGN PATENT DOCUMENTS

EP     2172259 A1     4/2010

OTHER PUBLICATIONS

PCT Notification of Transmittal of the International Search Report and the Written Opinion of the International Searching Authority, or the Declaration; dated Jun. 21, 2013; International Application No. PCT/US2013/028495; International File Date: Mar. 1, 2013.

*Primary Examiner* — Ana Fortuna
(74) *Attorney, Agent, or Firm* — Bracewell & Giuliani LLP; Constance Gall Rhebergen; Brad Y. Chin

(57) ABSTRACT

Certain embodiments of the invention provide an apparatus for separating aromatic hydrocarbons from an aromatic hydrocarbon feed stream. The apparatus includes a membrane support, and a hydrophilic polymer membrane matrix disposed on the membrane support. The hydrophilic polymer membrane matrix includes an effective amount of polyvinyl alcohol and an effective amount of sodium alginate. The apparatus further includes a carrier agent bonded to the hydrophilic polymer membrane matrix using a cross-linking agent. The carrier agent exhibits a greater affinity for aromatics compared to aliphatics. The apparatus further includes a membrane housing configured to hold the membrane support. The membrane housing includes an inlet, a permeate outlet, and a retentate outlet, the inlet being operable to receive the aromatic hydrocarbon feed stream, the permeate outlet being operable to discharge a permeate stream, and the retentate outlet being operable to discharge a retentate stream.

19 Claims, No Drawings

(56) References Cited

U.S. PATENT DOCUMENTS

| | | | |
|---|---|---|---|
| 5,670,051 A * | 9/1997 | Pinnau et al. | 210/651 |
| 5,670,052 A | 9/1997 | Ho et al. | |
| 6,187,987 B1 * | 2/2001 | Chin et al. | 585/819 |
| 6,786,796 B2 * | 9/2004 | Suto | 446/440 |
| 6,890,436 B2 * | 5/2005 | Komatsu et al. | 210/500.41 |
| 6,899,743 B2 | 5/2005 | Wijmans et al. | |
| 7,045,062 B1 * | 5/2006 | Aminabhavi et al. | 210/500.43 |
| 7,094,333 B2 | 8/2006 | Yang et al. | |
| 7,341,663 B2 | 3/2008 | Offeman et al. | |
| 7,638,053 B2 | 12/2009 | Yeager et al. | |
| 2002/0139719 A1 * | 10/2002 | Minhas et al. | 208/250 |
| 2003/0150795 A1 | 8/2003 | Dorgan et al. | |
| 2009/0020473 A1 | 1/2009 | Yeager et al. | |
| 2013/0228515 A1 * | 9/2013 | Yahaya | 210/640 |

* cited by examiner

FACILITATED TRANSPORT MEMBRANE FOR THE SEPARATION OF AROMATICS FROM NON-AROMATICS

BACKGROUND

1. Field of the Invention

Embodiments of the invention relate to a facilitated transport membrane (FTM), which is operable for separating aromatics from a hydrocarbon stream having both aromatics and aliphatic compounds.

2. Description of the Related Art

Aromatic hydrocarbons (e.g., benzene, toluene, xylenes (BTX)) serve as important precursors in the production of petrochemicals. Additionally, the separation of aromatics is useful in upgrading and conditioning aromatic-containing streams in petroleum refineries. Therefore, it would be helpful to provide a useful and economical method to help recover aromatics from all these streams.

Typical methods for separating aromatics from petroleum refineries can include liquid/liquid extraction and extractive or azeotropic distillation. However, these methods are typically very costly and capital intensive, For example, distillation columns are typically up to 300 feet tall and can contain over 200 trays. The reflux ratios are generally greater than 10 and the process is therefore very energy-intensive. As such, more economical separation processes are needed.

Membrane pervaporation processes have been used to separate various types of hydrocarbons. However, many of these conventional membranes suffer from low selectivity (i.e., 5 to 20) and/or a low flux rate (0.03-0.3 kg/m$^2$/h). Therefore, the commercial viability of conventional membranes is limited, preventing them from competing with conventional membrane pervaporation processes, such as extractive distillation. Therefore, it would be advantageous to have a FTM that has improved flux rates and/or selectivities over conventional membranes. It would also be advantageous if the FTM provided more strength and more stability than conventional membranes.

SUMMARY

Embodiments of the invention are generally directed to a FTM and a method for making and using the FTM. According to one embodiment, the FTM assists with the separation and recovery of high value aromatics from a hydrocarbon stream containing both aromatics and non-aromatics. In another embodiment, the FTM is combined with an extractive distillation process to provide further separation.

Various embodiments of the invention relate to the development of the FM and methods for making and using the FTM to separate and recover high value aromatics hydrocarbon from non-aromatic enriched streams, such as petroleum refinery, aromatic-containing streams, in a cost-effective manner. For example, in one embodiment, the FTM is obtained by incorporating complexing agents (i.e., carriers that exhibit a strong affinity for aromatics) on to the backbone or membrane matrix of a polymeric hydrophilic membrane, such that the complexing agents selectively interact with aromatics in the hydrocarbon feed, thereby significantly enhancing separation properties of the membrane compared with conventional polymeric membranes. The FTM exhibits excellent performance with significantly higher selectivity than convention membranes. In accordance with an embodiment, the FTM is operable to have a selectivity of at least about 40.

In accordance with another embodiment, the FTM is fabricated from a combination of glassy hydrophilic polymers, such as polyvinyl alcohol (PVA) and sodium alginate (SA). Silver salts, such as silver nitrate (AgNO$_3$) are used as the complexing agent (e.g., carrier) because it has a strong affinity for aromatics rather than aliphatics.

In accordance with another embodiment, an apparatus for separating aromatic hydrocarbons from an aromatic hydrocarbon feed stream is provided. The apparatus includes a membrane support, a hydrophilic polymer membrane matrix disposed on the membrane support, a carrier agent bonded to the hydrophilic polymer membrane matrix using a cross-linking agent, and a membrane housing configured to hold the membrane support. The hydrophilic polymer membrane matrix includes effective amounts of PVA and SA. The carrier agent may exhibit a greater affinity for aromatics compared with aliphatics. The membrane housing includes an inlet, a permeate outlet, and a retentate outlet. The inlet is operable to receive the aromatic hydrocarbon feed stream, the permeate outlet is operable to discharge a permeate stream, and the retentate outlet is operable to discharge a retentate stream. The apparatus is operable to separate aromatic hydrocarbons from non-aromatic hydrocarbons when the aromatic hydrocarbon feed stream is introduced into the membrane housing under membrane operating conditions.

In accordance with another embodiment, the carrier agent is selected from the group consisting of metal salts, amines and combinations thereof In another embodiment, the carrier agent includes AgNO$_3$. In a preferred embodiment, the AgNO$_3$ is incorporated into the hydrophilic polymer membrane matrix by creating a carrier solution of AgNO$_3$ in an amount of about 2 to about 15 weight percent mixed with an effective amount of a cross-linking agent, preferably about 5 weight percent, and water, preferably distilled water, in an amount of about 80 to about 93 weight percent, and then contacting the hydrophilic polymer membrane matrix with the carrier solution for an effective amount of time to bond the carrier agent with the hydrophilic polymer membrane matrix.

In accordance with another embodiment, the membrane support includes polyacrylonitrile. In another embodiment, the hydrophilic polymer membrane matrix includes an additional hydrophilic polymer selected from the group consisting of PVA, SA, polyacrylic acid, chitosan, polyacryl amide, polyvinyl amine and combinations thereof.

In accordance with another embodiment, the hydrophilic polymer membrane matrix is formed by obtaining a casting solution including the hydrophilic polymer and distilled water, and coating the membrane support with the casting solution. In one embodiment, the hydrophilic polymer includes PVA and SA. In another embodiment, the casting solution includes PVA in an amount from about 1 to about 5 weight percent, SA in an amount from about 1 to about 5 weight percent and the remainder being water.

In accordance with another embodiment, the cross-linking agent includes glutaraldehyde. In another embodiment, the membrane housing is any of the following: a spiral wound housing, a plate and frame housing, and a hollow-fiber bundled housing.

Certain embodiments of the invention also provide a method of making the FTM. For example, in accordance with an embodiment of the invention, the method for making the FTM includes the steps of obtaining a casting solution that includes a hydrophilic polymer and distilled water, coating a membrane support with the casting solution to form a hydrophilic polymer membrane, and drying the hydrophilic polymer membrane support. The method further includes the steps of obtaining the carrier solution that includes a carrier agent, a cross-linking agent, and distilled water; contacting the carrier solution to the hydrophilic polymer membrane support; and drying the membrane support. The FTM product is operable to separate aromatic components from non-aromatic components when the hydrocarbon stream having aromatic and non-aromatic hydrocarbons is introduced to the FTM under membrane operating conditions.

In accordance with one embodiment, the step of obtaining the carrier solution includes dissolving $AgNO_3$ in an amount from about 2 to about 15 weight percent with glutaraldehyde in an amount of about 5 weight percent, with the remainder being distilled water. In another embodiment, the hydrophilic polymer is selected from the group consisting of PVA, SA, polyacrylic acid, chitosan, polyacryl amide, polyvinyl amine and combinations thereof.

in accordance with another embodiment, the step of obtaining the casting solution includes dissolving up to 5 weight percent of the hydrophilic polymer in distilled water. In another embodiment, the step of obtaining the casting solution includes dissolving PVA in an amount from about 1 to about 5 weight percent with SA in an amount from about 1 to about 5 weight percent, with the remainder being distilled water.

Certain embodiments of the invention further provide a method for using the FTM to separate aromatic components from non-aromatic components in a hydrocarbon stream. In one embodiment, the method for using the FTM to separate aromatic components includes the step of feeding the hydrocarbon stream including aromatic components and non-aromatic components into an inlet of any of the apparatuses described herein under membrane operating conditions, such that at least a portion of the aromatic components diffuse across the hydrophilic polymer membrane matrix. The method further includes the steps of withdrawing a permeate stream enriched in aromatic components compared with the hydrocarbon stream through the permeate outlet, and withdrawing a retentate stream enriched in non-aromatic components compared with the hydrocarbon stream through the retentate outlet.

In accordance with another embodiment, the method further includes the step of introducing the retentate stream to a distillation column under distillation conditions to remove additional aromatic components to form a lean, non-aromatic stream and a lean aromatic stream. In another embodiment, the membrane operating conditions include operating conditions normally encountered during pervaporation. In another embodiment, the hydrocarbon stream is in a liquid phase.

DETAILED DESCRIPTION

Although the following detailed description contains many specific details for purposes of illustration, it is understood that one of ordinary skill in the relevant art will appreciate that many examples, variations, and alterations to the following details are within the scope and spirit of the invention. Accordingly, the exemplary embodiments of the invention described herein are set forth without any loss of generality, and without imposing limitations, relating to the claimed invention.

Certain embodiments of the invention are directed to a FTM prepared from hydrophilic polymers. The FTM is useful in the separation of aromatic and non-aromatic hydrocarbons from mixtures containing such hydrocarbons. Other embodiments of the invention are directed to a process for preparing the FTM, which includes contacting polymers of the FTM with an effective amount of a cross-linking agent under membrane operating conditions to promote cross-linking of the polymers, thereby forming a cross-linked polymer membrane. In accordance with various embodiments of the invention, the cross-linked polymer membrane exhibits selectivity for aromatic hydrocarbons.

In accordance with an embodiment, suitable hydrophilic polymers that may be used to prepare the FTM include PVA and SA. In another embodiment, an additional hydrophilic polymer includes one or more of the following: poly-acrylic acid, chitosan, polyacryl amide, and polyvinyl amine, Preferably, the hydrophilic polymers of the present invention are selected such that the hydrophilic polymers undergo cross-linking in the presence of an effective amount of the cross-linking agent under suitable membrane operating conditions.

Certain embodiments focus on the development of the FTM. Optionally, the FTM membrane is combined with an extractive distillation process for separating and recovering high value aromatics in a more cost effective fashion. In one embodiment, aromatic-containing streams from petroleum refineries are used as a hydrocarbon feed. Other acceptable sources for hydrocarbon feed include naphtha cracker feed streams, transportation gasoline fuel mixture feedstock and reformate effluent streams, as non-limiting examples.

Furthermore, in one embodiment, the FTM is obtained by incorporation of complexing agents or carriers (i.e., that exhibit a strong affinity for aromatics) on to the backbone or membrane matrix of the hydrophilic polymeric membrane. The complexing agents are operable to selectively interact with aromatics in the mixture. In accordance with an embodiment, the FTM is operable to have a selectivity of at least about 40.

In another embodiment, the membrane operating conditions includes pervaporation and perstraction. Pervaporation employs a vacuum (i.e., lowered pressure) on the permeate side of the membrane in order to remove permeated compounds, while perstraction employs a liquid or gas sweep stream to carry away the permeate. Thus, unlike conventional distillation processes and other conventional extraction processes, the separation mechanism in pervaporation or perstraction is not based on the relative volatility of components, rather the separation mechanism is based on the difference between the sorption and diffusion properties of the feed substances and the permselectivity of the FTM.

in one embodiment, the FTM is useful for the separation of aromatics, including sulfur and nitrogen heteroatom cyclic compounds, from non-aromatics in petroleum and chemical streams, and has been found to be particularly useful for the separation of large substituted aromatics from saturates. Typical feed streams include heavy catalytic naphtha streams, intermediate catalytic naphtha streams, light aromatics content streams, light catalytic cycle oil, jet fuel, diesel and streams in chemical plants that contain recoverable quantities of BTX or other aromatics in combination with saturates.

In one embodiment, the membrane itself may be in any convenient form utilizing any convenient module design. Thus, sheets of membrane material may be used in spiral wound or plate and frame permeation cell modules. Hollow fiber housings of membranes may be used in bundled configurations with either the feed or the sweep liquid (or vacuum) in the internal space of the tube or fiber; the other material being on the other side.

In an additional embodiment, the use of the FTM could be integrated before or after a separate extractive distillation process. If used prior to the distillation process, the FTM allows for greater product yields or quality from the existing column due in part to the tower amounts of feedstreams being processed. If used following the distillation process, the FTM acts as polishing step of either the top or bottom product of the distillation column, especially when high purity products are required.

The FTM according to various embodiments of the invention provides non-obvious advantages over conventional membranes. For example, the FTM according to at least one embodiment of the invention provides a FTM, which is operable for separating aromatics from a hydrocarbon stream having both aromatics and aliphatic compounds, and a process for making and using the FTM, which reduce investment and operating costs associated with aromatic separation from the hydrocarbon stream due to savings from reduced energy consumption required by the overall process and a reduction of cost for membrane replacement.

EXAMPLES

The following examples are given for the purpose of illustrating embodiments of the present invention, However, it is to be understood that these examples are merely illustrative in nature, and that the process embodiments of the present invention are not necessarily limited thereto.

A hydrocarbon feed containing both aromatic and aliphatic compounds was prepared having a 1:4 ratio of benzene to cyclohexane. Cyclohexane was used as a representative of an aliphatic compound because its size and boiling point are similar to benzene. The membrane housing was created using a cell, separated into two compartments by a porous metal plate (i.e., a membrane support) with the hydrophilic polymer membrane matrix being disposed on the porous metal plate. The membrane housing was attached via a pump through a 5 L reservoir tank filled with a liquid mixture of the benzene-cyclohexane solution. The feed solution of known composition was pumped past the feed side of the membrane cell and then returned back to the reservoir tank at a controlled flow rate. The benzene concentration in the reservoir was measured versus time with a gas chromatograph (e.g., Varian 3300) equipped with a thermal detector and integrator. Trans-membrane fluxes were generated by a downstream vacuum pump and the permeation measurement was carried out under vacuum on the downstream side of the membrane. The upstream pressure was maintained at atmospheric pressure. The other side of the membrane housing was normally attached through a liquid nitrogen cold trap to a vacuum pump to condense and collect the permeate vapor. The weight and concentration of the accumulated permeate in the cold trap were also determined with time by measurement of sample weight collected and by gas chromatography analysis, respectively. In a typical pervaporation experiment, membrane fluxes were allowed to stabilize for about two to three hours before permeate samples were collected over a period of about one to three hours. The experiments were performed for permeate pressure of 0.2 mmHg, temperature of 30° C. and for different polymeric membrane types.

In order to create the hydrophilic polymer membrane matrix, several casting solutions were prepared by dissolving various amounts of PVA and SA separately in distilled water at about 90° C. to make a homogeneous solution for each polymer. A carrier solution was prepared by mixing amounts between 2 to 15 weight percent $AgNO_3$ and 5 weight percent of a glutaraldehyde (GA) cross-linking agent in distilled water. The casting solutions were then coated On the membrane support (PAN) and left to dry over night. The coated membrane was then dipped in the carrier solution for about 5 mins and then taken out to dry over night. The composite membrane became dark green upon dipping it in the cross-linking and carrier solution, The compositions of the four membranes are provided in Table I below:

TABLE I

Compositional Make-up of the Membranes

| Membrane Formulation | Casting Solution Composition | Carrier Solution Composition |
|---|---|---|
| A | 5 wt % PVA | 15% $AgNO_3$ |
| B | 2.5 wt % PVA; 2.5 wt % SA | 2% $AgNO_3$ |
| C | 1 wt % PVA; 2.5 wt % SA | 2% AgNO3 |
| D | 5 wt % SA | 2% AgNO3 |

The prepared FTMs were tested with feed concentration of 1:4 (wt/wt) benzene:cyclohexane in the membrane housing described above with the permeate side kept under vacuum. The results are provided in Table II below:

TABLE II

Experimental Results for Various Membrane Formulations

| Membrane Formulation | Benzene Conc. in permeate (wt %) | Flux (kg/(m²hr)) | Separation factor |
|---|---|---|---|
| A | 93 | 0.018 | 53 |
|   | 88 | 0.017 | 29 |
|   | 92 | 0.019 | 46 |
| B | 89 | 0.014 | 32 |
|   | 90 | 0.013 | 36 |
|   | 92 | 0.013 | 46 |
| C | 32 | 0.1 | 1.9 |
|   | 29 | 0.05 | 1.6 |
| D | 83 | 0.01 | 19.5 |

The flux was calculated based on the following equation:

$$q = \frac{m}{A*t}$$

where q is the flux, m is the mass of the permeate fluid (kg), A is the cross sectional area of the effective membrane (m$^2$), t is time (hour).

The total benzene-cyclohexane flux was determined from the liquid collected in the cold trap, the time of collection, and the membrane surface area in contact with the feed solution. The individual benzene and cyclohexane fluxes were calculated from the total flux and the benzene concentration.

The separation factor of the process was determined by the following equation:

$$\alpha = \frac{[C_a]_p/[C_n]_p}{[C_a]_f/[C_n]_f}$$

where $[C_a]_p$ the concentration of benzene in the permeate, $[C_n]_p$ is the concentration of cyclohexane in the permeate, $[C_a]_f$ is the concentration of benzene in the feed, and $[C_n]_f$ is the concentration of cyclohexane in the feed.

The present invention may suitably comprise, consist or consist essentially of the elements disclosed and may be practiced in the absence of an element not disclosed. For example, it can be recognized by those skilled in the art that certain steps can be combined into a. single step.

Unless defined otherwise, all technical and scientific terms used have the same meaning as commonly understood by one of ordinary skill in the art to which this invention belongs.

The singular forms "a", "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

I claim:

1. An apparatus for separating aromatic hydrocarbons from an aromatic hydrocarbon feed stream, the apparatus comprising:
    a membrane support;
    a hydrophilic polymer membrane matrix disposed on the membrane support, the hydrophilic polymer membrane matrix comprising polyvinyl alcohol and sodium alginate;
    a carrier agent bonded to the hydrophilic polymer membrane matrix using a cross-linking agent, the carrier agent exhibiting a greater affinity for aromatics compared to aliphatics; and
    a membrane housing configured to hold the membrane support, the membrane housing comprising an inlet, a permeate outlet, and a retentate outlet, the inlet being operable to receive the aromatic hydrocarbon feed stream, the permeate outlet being operable to discharge a permeate stream, and the retentate outlet being operable to discharge a retentate stream,
    wherein the apparatus is operable to separate aromatic hydrocarbons from non-aromatic hydrocarbons when the aromatic hydrocarbon feed stream is introduced into the membrane housing.

2. The apparatus as claimed in claim 1, wherein the carrier agent is selected from the group consisting of metal salts, amines and combinations thereof.

3. The apparatus as claimed in claim 1, wherein the carrier agent is bonded to the hydrophilic polymer membrane matrix by obtaining a carrier solution and contacting the carrier solution with the hydrophilic polymer membrane matrix, the carrier solution comprising silver nitrate in an amount from about 2 to about 15 weight percent and glutaraldehyde in an amount of about 5 weight percent with water.

4. The apparatus as claimed in claim 1, wherein the membrane support comprises polyacrylonitrile.

5. The apparatus as claimed in claim 1, wherein the hydrophilic polymer membrane matrix further comprises an additional hydrophilic polymer selected from the group consisting of polyacrylic acid, chitosan, polyacryl amide, polyvinyl amine, and combinations thereof.

6. The apparatus as claimed in claim 1, wherein the hydrophilic polymer membrane matrix is disposed on the membrane support by coating the membrane support with a casting solution, the casting solution comprising polyvinyl alcohol in an amount from about 1 to about 5 weight percent and sodium alginate in an amount from about 1 to about 5 weight percent with water.

7. The apparatus as claimed in claim 1, wherein the cross-linking agent comprises glutaraldehyde.

8. The apparatus as claimed in claim 1, wherein the membrane housing is selected from the group consisting of a spiral wound housing, a plate and frame housing, and a hollow-fiber bundled housing.

9. The apparatus as claimed in claim 1, wherein the hydrophilic polymer membrane matrix is operable to have a selectivity of at least about 40 for aromatic hydrocarbons.

10. A method for using a facilitated transport membrane to separate aromatic components from non-aromatic components, the method comprising:
    feeding a hydrocarbon stream comprising aromatic components and non-aromatic components into the inlet of the apparatus of claim 1 under membrane operating conditions such that at least a portion of the aromatic components diffuse across the hydrophilic polymer membrane matrix;
    withdrawing a permeate stream enriched in aromatic components compared to the hydrocarbon stream through the permeate outlet; and
    withdrawing a retentate stream enriched in non-aromatic components compared to the hydrocarbon stream through the retentate outlet.

11. The method as claimed in claim 10, further comprising:
    introducing the retentate stream to a distillation column under distillation conditions to remove additional aromatic components to form a lean non-aromatic stream and a lean aromatic stream.

12. The method as claimed in claim 10, wherein the membrane operating conditions comprise pervaporation conditions.

13. The method as claimed in claim 10, wherein the hydrocarbon stream is in a liquid phase.

14. A method of making a facilitated transport membrane, the method comprising:
    obtaining a casting solution comprising a hydrophilic polymer and distilled water, the hydrophilic polymer comprising polyvinyl alcohol and sodium alginate;
    coating a membrane support with the casting solution to form a hydrophilic polymer membrane support;
    drying the hydrophilic polymer membrane support after the step of coating;
    obtaining a carrier solution comprising a carrier agent, a cross-linking agent, and distilled water;
    contacting the carrier solution to the hydrophilic polymer membrane support after the step of drying the hydrophilic polymer membrane support; and
    drying the hydrophilic polymer membrane support after the step of contacting the carrier solution to form the facilitated transport membrane, the facilitated transport membrane being operable to separate aromatic components from non-aromatic components when a hydrocarbon stream comprised of aromatic and non-aromatic hydrocarbons is introduced to the facilitated transport membrane under membrane operating conditions.

15. The method as claimed in claim 14, wherein the carrier agent is selected from the group consisting of metal salts, amines and combinations thereof.

16. The method as claimed in claim 14, wherein the obtaining the carrier solution further comprises dissolving silver nitrate in an amount from about two to about fifteen weight percent with glutaraldehyde in an amount of about five weight percent in distilled water.

17. The method as claimed in claim 14, wherein the obtaining the casting solution further comprises dissolving from 2 to 5 weight percent of the hydrophilic polymer in distilled water.

18. The method as claimed in claim 14, wherein the obtaining the casting solution further comprises dissolving polyvinyl alcohol in an amount from about 1 to about 5 weight percent with sodium alginate in an amount from about 1 to about 5 weight percent in distilled water.

19. The method as claimed in claim 14, wherein the membrane operating conditions comprise pervaporation conditions.

\* \* \* \* \*